United States Patent [19]

Meyer

[11] Patent Number: 4,549,319
[45] Date of Patent: Oct. 29, 1985

[54] ARTIFICIAL JOINT FIXATION TO BONE

[75] Inventor: Benjamin S. Meyer, Birmingham, Ala.

[73] Assignee: United States Medical Corporation, Washington, D.C.

[21] Appl. No.: 404,774

[22] Filed: Aug. 3, 1982

[51] Int. Cl.[4] ............................................. A61F 1/04
[52] U.S. Cl. .................................. 623/22; 128/92 C; 623/18
[58] Field of Search ............ 3/1.9, 1.91, 1.912, 3/1.913; 128/92 C, 92 CA

[56] References Cited

U.S. PATENT DOCUMENTS

| Re. 28,895 | 7/1976 | Noiles | 3/1.913 X |
|---|---|---|---|
| 2,719,522 | 10/1955 | Hudack | 128/92 CA |
| 3,820,167 | 6/1974 | Sivash . | |
| 3,848,276 | 11/1974 | Martinez . | |
| 3,855,638 | 12/1974 | Pilliar . | |
| 3,943,576 | 3/1976 | Sivash . | |
| 3,996,625 | 12/1976 | Noiles . | |
| 4,068,324 | 1/1978 | Townley et al. | 3/1.913 |
| 4,077,070 | 3/1978 | Sivash . | |
| 4,219,983 | 9/1980 | Noiles . | |
| 4,406,023 | 9/1983 | Harris | 3/1.912 |

FOREIGN PATENT DOCUMENTS 10527   4/1980   European Pat. Off. .

Primary Examiner—Richard J. Apley
Assistant Examiner—Isabella David
Attorney, Agent, or Firm—Fleit, Jacobson, Cohn & Price

[57] ABSTRACT

A joint prosthesis for fixation to the bone having a joint motion element and a stem attached thereto and extending into the central canal of the bone into which the prosthesis is to be fixed. That part of the prosthesis at the end of the bone located near the joint motion element defining an external geometric pattern of elongated projections spaced circumferentially around the prosthesis which engages with the bone when implanted thereby establishing a tight fit between the prosthesis and the bone.

7 Claims, 14 Drawing Figures

ARTIFICIAL JOINT FIXATION TO BONE

BACKGROUND OF THE INVENTION

1. Field of the Invention

The present invention relates to the fixation, or fastening, of artificial joint components.

Presently, orthopedic surgeons most commonly use polymethyl methacrylate (PMMA) cement for fixing artificial joint components to bone. This technique has the advantage that high fixation strength is attained immediately post operatively. The patient can undertake physical activity involving the newly implanted joint within a few days post operatively. This is beneficial for the patient's physical well being because it stimulates circulation and respiration.

However, joint implantation using the PMMA cement has not been entirely satisfactory in the long term. Artificial joints, and their fixation, must withstand large mechanical forces. Especially so in the weight bearing joints: hip, knee and ankle. Transfer of these large mechanical forces from the prosthetic joint to the bone is through a complex structural system when cement is employed. The tensile and compression strengths and the moduli of elasticity vary greatly among the elements in this system: bone, cement and prosthesis. When the prosthesis is metal, the cement is the least strong and the least stiff of the three. The cement is also subject to brittle failure. Failure of prosthetic joint implants is often traceable to failure in the cement fixation. Many hip femoral prosthesis stems have fractured after the supporting cement interface has failed in one way or another. The cement is particularly vulnerable to failure in the proximal femur because this is usually the region of maximum force transfer from the prosthesis to the bone.

Because of the demonstrated long term inadequacy of prosthetic fixation using cement, it has been a continuing objective to achieve direct fixation between the prosthetic structural component and bone. Numerous attempts to achieve this goal have been made over many years. Investigators have employed or proposed:

- metal components press fit impacted into prepared bone canals or cavities. These components were tapered pins with both smooth or irregular surfaces, acetabular cups with "petals" or teeth for cutting into the bone, or stems with sintered porous metal surfaces. See for instance U.S. Pat. No. 3,996,625 entitled Artificial Hip Joint with Novel Stem issued to Douglas G. Noiles on Dec. 14, 1976, and U.S. Pat. No. 3,855,638 entitled Surgical Coating issued to Robert M. Pilliar on Dec. 24, 1974.
- metal components with porous plastic coatings of several kinds.
- metal components with surfaces of a fibrous metal composite, which coating is made from a compressed and sintered metal fiber mesh.
- metal components coated with biologically active and accepted glassy material, sometimes called a "bioglass" coating.
- porous plastic elements have been tried but their mechanical strength is very low.
- ceramic components with and without porous or threaded surfaces, and with biologically active ionic surface treatments.
- metal components with threaded stems, and threaded ceramic acetabular cups.

Use of most of the above structures and methods does not permit the initial implantation to achieve intimate mechanical load transmitting relationships between the prosthesis and bone. That is, they are intended to permit bone ingrowth into the porosities or irregularities of the surface of the prosthesis. This bone ingrowth phenomenon is reported to take place in about one to five months in order to achieve adequate structural strength for patient physical activity involving the affected joint. During this time the prosthesis-to-bone interface must be maintained without motion, because it is known that motion at this interface will cause the body to develop soft non-bony tissue at this interface which provides inadequate support for the prosthesis. Therefore, most of the above proposed techniques anticipate restricted patient activity for extended periods. Such restricted activity is not desired for reasons of the patient's overall physical health.

The above mentioned threaded prosthetic stem concept can provide initial intimate load bearing prosthesis-to-bone interface. However, the threaded stem has surface discontinuities which reduce the fatigue endurance strength of the prosthetic component. There are additional difficulties in screwing into the prepared bony canal or cavity the entire prosthetic component to achieve the correct depth of insertion and angle of orientation. For instance, a part of the prosthesis may interfere with a part of the bone when attempting to screw the prosthesis into position.

Results of recent experience with prosthetic joint components with porous metal surfaces which foster bone ingrowth have confirmed that bone reshapes and redensifies itself, by a behavior called "remodeling", to suit the path of load transmission from the prosthesis to the bone. This same experience also demonstrates that it is desirable to transfer a maximum fraction of the total load as close as possible to the normal joint surface in order to encourage the retention of a maximum amount of normal bone mass. For example, a femoral stem prosthesis for a hip joint which provides for bone ingrowth at the distal end of the stem may promote load transfer at that part of the prosthesis with the result that the bone adjacent to the proximal part of the stem will not carry a physiological share of the total load and therefore will become less dense and less strong. While a prosthesis so fixed may function satisfactorily, such a biological change is undesired in the event that the femoral stem prosthesis ever has to be replaced, for any of a number of reasons, in which case the surgeon is forced to deal with an abnormally reduced amount of bone stock in the proximal femur.

There are three principles which are generally accepted to apply to the successful fixation of joint prostheses by direct bone contact and support of the prosthesis. One, the prosthesis must be in contact with sound bone. That is, the bone to which force is transmitted by the prosthesis must have adequate strength to support the applied stresses. This implies that the stress applied to the bone will be within the physiological stress carrying capability of the bone. Two, the prosthesis must be a good fit in the prepared bony cavity. And three, there must not be motion between the prosthesis and the bone.

It is clear that the above three requirements are closely interrelated and very much dependent on favorable geometric relationship between the prosthesis and the bone. It must be true that if a patient's joint and bone structure functioned to any reasonable extent prior to implantation of a prosthesis, then the patient's bone quality is somewhere adequate to support the loads due to that degree of function of that particular joint. The problem then becomes one of providing a prosthesis of the correct shape and size to contact the patient's bone at the optimum interface surface for satisfactory transfer of force from the prosthesis to the bone. Further, the prosthesis must satisfy the above and also fill the space created in the bone with the utmost of congruency in order to inhibit motion between the prosthesis and the bone. It has been reported that bone may grow to fill spaces adjacent the implant of up to 2 mm. Certainly, spaces however small between the implants and the bone do not favor the necessary absence of motion therebetween. Because humans vary so remarkably in physical size and shape, we begin to see that each prosthesis should be custom sized and shaped to suit the bone into which it is to be implanted. Aside from the economic cost of providing a custom prosthesis for each joint of each patient, there is an overriding practical impediment to so doing. The exact dimension for an optimum size and shape of prosthesis cannot be determined before the time of surgery when the bone is opened and its true nature is learned.

The truth of the above may be substantiated by the relative success to date of implantation of joint prostheses using polymethyl methacrylate cement. The cement serves the function of providing a custom prosthesis for the individual bone at the time of implantation. The bone is opened, explored, reamed and broached to create a cavity which is surrounded by bone judged by the surgeon to be of adequate strength to support the forces to be received by the bone. The basic prosthesis, usually metal, is available in an assortment of shapes and sizes, perhaps as many as two dozen. The ulilization of PMM cement to fill the spaces between the prosthesis and the bone is, in fact, the creation of a custom prosthesis for that particular implantation. The mechanical properties of the cement are inadequate to provide a satisfactorily high percentage of successful implants for long term use, however.

Accordingly, a primary object of the present invention is to provide means for fastening a load bearing component of an artificial joint prosthesis to the host's bone in a manner which accommodates a pattern of load transfer from the prosthesis to the bone where a maximum fraction of the total load is transferred to that part of the bone nearest the normal joint surface, by which the prosthetic component provides increased interface load transmitting area of contact with the bone at this subject area.

An additional primary object is to provide a system of components for artificial joint prostheses where a number of variations of sizes and shapes for each component can be combined to create a much larger number of combinations in size and shape of prosthesis assemblies and thereby permit the selection of optimum fit between the prosthesis and the bone at the time of surgery.

An additional primary object is to provide means for fastening intimately the load bearing component of an artificial joint prosthesis with high initial fastening strength without the use of PMMA cement in that part of the bone nearest the joint motion surface, while also permitting the critical structural load bearing component to have generous physical dimensions and contours which either add to, or do not diminish, the fatigue endurance strength of the prosthesis.

A further object is to provide a system which facilitates achieving the correct geometric orientation of the load bearing components to the bone which is independent of the firmness of seating of the fastening means.

A further object is to provide the above advantages while using materials of high biological compatibility, structural strength and elastic compliance.

A further object is to provide a system for prosthesis fixation which is compatible with present day orthopedic surgical practice.

A further object is to provide instruments for use in achieving prosthesis fixation to bone according to this invention.

SUMMARY OF THE INVENTION

The present invention for implantation of an artificial joint prosthesis derives from a consideration of the three principal distinct types of force which may be transmitted from a structural component of a joint prosthesis to the host's bone, the recognized desirability of transferring a maximum part of the total load to that part of the bone which is closest to the joint motion surface, and the additional desirability of not using PMMA cement in that part of the bone which is closest to the joint motion surface, while at the same time providing immediate fixation with sufficient initial strength to prevent motion between the prosthesis and the bone during early physical rehabilitation of the patient. It is further desirable to provide a prosthesis to bone fixation geometry which disrupts the normal physiological blood flow pattern to the minimum possible extent. It is recognized that the strength of fixation will increase with time as the bone remodels itself to accomodate the new stress pattern created by the implantation of the prosthesis if there is no motion between the prosthesis and the bone.

The three principal types of forces transmitted between the prosthesis and the bone are compression, torsion and bending. While tensile forces do exist in the weight bearing bones, they are generally the result of bending. It is highly unlikely that a joint prosthesis would transmit a net tensile force to the bone. Further, the present invention contemplates the transmission of tensile force from the prosthesis to the bone, as will be discussed later.

The invention will be described as embodied in a hip joint prosthesis of the proximal femur although it is applicable to any joint prosthesis including but not limited to those for a shoulder, elbow, wrist, knee, ankle, finger and toe. The hip prosthesis is provided with a stem which extends into the canal of the femur for a distance of approximately 5 to 8 inches, although this could be longer should conditions dictate. The stem carries a collar or flange, transverse to the stem, which abuts the excised proximal end of the femur where the head and neck of the natural femur have been excised for implantation of the prosthesis. Proximal of the collar the prosthesis comprises a neck portion which supports the ball or head of the prosthesis at a distance from the extended centerline of the shaft of the femur.

The stem also carries a number of relatively short longitudinal fins or splines adjacent to the flanges on the side of the flange opposite from the hip joint, which fins are, at the time of implantation, embedded in the prepared cancellous bone which exists at the end of the bone adjacent the joint surface. Some of the outer edges of the fins may contact and cut into the inside of the cortical wall of the bone which surrounds the cancellous bone. The side of the flange which is in contact with bone and all of the surfaces of the fins may be coated with a porous sintered metal layer or any other textured or treated surface designed to enhance fixation to bone.

The force of compression is transferred from the prosthesis to the bone principally by means of the collar which abuts the excised proximal end of the femur. The collar is preferably shaped to contact essentially all of the excised surface, which is more or less transverse to the shaft of the bone.

The force applied to the femoral prosthesis is exerted downward on the head of the prosthesis by the acetabulum or socket of the hip joint, and passes through the center of the ball. When the line of action of this force intersects the centerline, or extended centerline of the femoral canal, or is parallel to this centerline, the forces transmitted from the prosthesis to the bone are limited to those of compression and bending. When the line of action of this force is other than just described, then there is a component of this force which must be transmitted from the prosthesis to the bone as torque. That is, any force applied to the head of the prosthesis whose line of action is not in a plane which contains the centerline of the femoral canal will create a torque about this centerline.

The short longitudinal fins or splines on the stem and emanating from the collar are driven into the prepared cancellous bone of the femur adjacent to the excised surface of the femur to establish a tight fit therein at the same time the collar abuts the excised surface. The numerous fins provide a relatively large surface area through which torque is transmitted from the prosthesis to the bone at that part of the bone closest to the joint surface. The fins act as keys to prevent the prosthesis from rotating about the axis of the shaft of the femur. The applied torque is resisted by compression and shear forces which are distributed throughout a large volume of the cancellous bone.

Finally, the bending component of the force system will be transmitted from the prosthesis to the bone by two opposed forces, one of which acts perpendicular to the centerline of the femoral shaft at the proximal end of the femur, essentially in the area occupied by the finned part of the stem; and the other of which acts perpendicular to the centerline of th femoral shaft at the distal end of the prosthesis. The bending component is a large part of the complete force system, and the forces which constitute the two forces described above will be larger if the distance between them is small.

Preferably the part of the prosthetic stem contained within the bone will be 5 to 8 inches long. This length creates reaction forces to bending which will not exceed the acceptable load capacity of the bone which envelopes the stem. Also, it is preferred that the surface of the distal end of the stem not transmit the force components of axial compression or torque from the prosthesis to the bone, therefore this surface should not be textured, coated or treated to enhance transfer of shear loads at the surface interface with the bone. It is important that the distal stem fit securely within the femoral canal to prevent any transverse movement between the prosthesis and the bone. It is also contemplated that polymethyl methacrylate cement can be used advantageously to fix the distal prosthesis stem in the canal of the femur. The inventive structure limits the load transfer at this point to a reaction force to bending. That is, the principal stress in cement so used will be in compression between the prosthesis stem and the wall of the canal of the femur. The cement is satisfactory for this type loading. This technique adds to the ability to provide custom fit with a limited number of component sizes.

On the other hand, the surfaces of the collar and the fins are preferably textured, coated or treated to enhance transfer of shear loads at the prosthesis-to-bone interface in this area. It can be seen that such transfer of shear loads will contribute to maximizing the transfer of all three load type components to the proximal bone of the femur. The fins will thus transmit some of the pure compression load as well as some of the compression and tension loads resulting from bending. The underside of the collar can transmit a part of the torque by transmitting shear forces at the collar-to-bone interface. The function of the fins will not be diminished if some of the fins at this outer edge contact the cortical wall of the femur. In fact, this circumstance may be beneficial.

Additionally, it is known that the principal avenues of blood supply within the femur are longitudinal. The longitudinal fins provide the advantage of providing a multitude of paths for stress transfer from prosthesis to bone in the proximal femur with a minimum disruption of the blood supply within the femur, while also permitting the regeneration of physiologically desirable longitudinal blood paths.

Because human bones come in an endless variety of diameter, length, wall thickness, taper, curvature, etc., an alternative construction is proposed which has the greater practical utility. In this alternative embodiment, the collar and longitudinal fins are integral with a thin wall truncated conical sleeve. The large end of the sleeve carries the collar which extends radially outward. The surfaces of the sleeve which contact bone may be textured, coated or treated to enhance fixation to the bone. Or, the entire sleeve may advantageously be made from a suitable porous metal.

With the alternative sleeve embodiment, the femoral component has no collar or fins. The shaft of the stem is smooth and tapered to lock within the sleeve by the well known principle of mechanical tapers. This embodiment offers the advantage of permitting a variety of size selections for the sleeve component and for the stem component separately. Thus a smaller number of total components is needed to achieve a given number of total size combinations for the final assembly. The two component embodiment may be more economical to manufacture, and will conveniently allow selection of size and implantation of the sleeve before the stem is implanted.

With either of the above embodiments, one aspect of preparation of the femur consists in reaming the intramedullary canal to a cross sectional shape and size and to a depth to accept the shaft of the stem of the prosthesis so that the distal part of the prosthesis will be securely held within the femur without the possibility of transverse motion between the prosthesis and the bone. There must be a selection of sizes of reamers, and a selection of sizes for the distal stem of the prosthesis so that the above condition of fit is obtained. Alternatively or concurrently, use of PMMA cement may be advantageously confined to fixing the distal prosthetic stem in the femoral canal as described above.

A second aspect of preparation of the femur consists in creating an essentially transverse surface of the proximal femur against which the collar will abut to lie in a plane which is the same as the plane which the underside of the collar will define when the prosthesis is implanted. A bone cutter and guide can be provided to permit this condition to be obtained. A selection of prosthetic components with varied collar areas must be available so that one can be chosen which will closely match the shape of the bone against which the collar fits. The prosthesis is intended to be implanted with the collar fully seated against the mating bone.

A third aspect of preparation of the femur consists in broaching multiple slots into the cancellous bone of the proximal femur, which slots are to accommodate by press or impacted fit the multiple fins of the prosthesis. A selection of sizes of broaches must be available so that the slots can extend radially as much as the particular femur will allow. A selection of prostheses with various sizes of multiple fin envelopes must also be available to correspond to the several sizes of broaches so that the prepared slots can be filled with fins in tight proximity to cancellous bone, and in some areas the edges of some of the fins will be in tight proximity to the cortical wall of the femur. If the slots in the bone are each 1.5 mm wide, each fin will be somewhat thicker, say 1.6 mm to 1.7 mm thick, so that the fins must be driven into the slots. In this manner the proximal femur is immediately in a preloaded fit to the prosthesis and motion between the prosthesis and the bone is prevented during the early physical rehabilitation of the patient. Angular location of the broached slots is made consistent with the desired angular orientation of the neck of the prosthesis in the final implanted condition, if the embodiment requires.

Alternatively, the longitudinal fins can be made self-broaching and a selection of prostheses provided with the volume envelope of the fins increasing in a series of sizes. Successive prostheses are driven into the femur bone and removed to be replaced by the next larger prosthesis until the desired security of fit achieved. This technique is preferred to be used with the thin walled sleeve construction.

Thus the implantation of either embodiment provides initial mechanically strong fixation to resist motion between the prosthesis and the bone which could result from the three principal forces. Motion due to compression is resisted by contact between the collar and the excised surface of the bone, including the cortical margin of the bone, especially the region known as the calcar. Motion due to torque is resisted by the many securely implanted fins in the relatively large volume of cancellous bone in the proximal femur, as well as by some engagement between the edges of some fins and the cortical wall. Motion due to bending is resisted by a large fraction of the fins in the proximal cancellous bone at the one force and reaction area, and by the secure fit of the distal stem in the femoral canal at the second force and reaction area.

The initial fixation is strong enough to prevent motion between the prosthesis and the bone during post operative recuperation and rehabilitation. As stated above, motion between the prosthesis and the bone will cause the development of soft non-bony tissure which is inadequate to support the prosthesis.

Because it is a principle of physiology that bone develops shape and density according to the manner in which load is imposed on it, and because the prosthesis will transmit force to the bone in a manner different from that imposed by the original natural joint, it is true that the bone will have to reshape and redensify itself before the new prosthetic joint-to-bone fixation achieves maximum strength. This is true whenever the pattern of force application to bone is changed.

The advantages of the prosthesis of this invention are fourfold. One, the prosthesis is designed, sized and installed with immediate load bearing juxtaposition between the several elements of the prosthesis and the associated bone. Bone does not have to grow into the spaces between the fins as it has to grow into the interstices of porous or other irregular surfaces. Two, PMMA cement is not used in the highly loaded part of the bone nearest the joint motion surface. This is the area where the use of cement has proven to be the least successful. Three, with a planned and controlled program of increasing patient activity, the bone remodels itself to accommodate the new force patterns and the fixation becomes stronger the more it is used. It is to be emphasized that the prosthesis transmits a maximum of load and stress to the bone at the most proximal part of the femur, so that the density and strength of this proximal bone may be preserved. Fourth, the prosthesis creates a minimum disruption of the normal blood supply paths within the proximal femur.

The material of the prosthesis must be biologically acceptable to the development of bone in intimate contact with the prosthesis. Preferably the prosthesis is made of titanium alloy, specifically an alloy known as Ti6AL4V. This alloy is highly resistant to corrosion and is well tolerated by the body. It has high mechanical fatigue endurance strength and a modulus of elasticity, or stiffness characteristic which, while approximately five times greater than that of bone, is approximately half that of other metals commonly used in artificial joint prosthesis.

DESCRIPTION OF THE PREFERRED EMBODIMENTS

Figure 1:
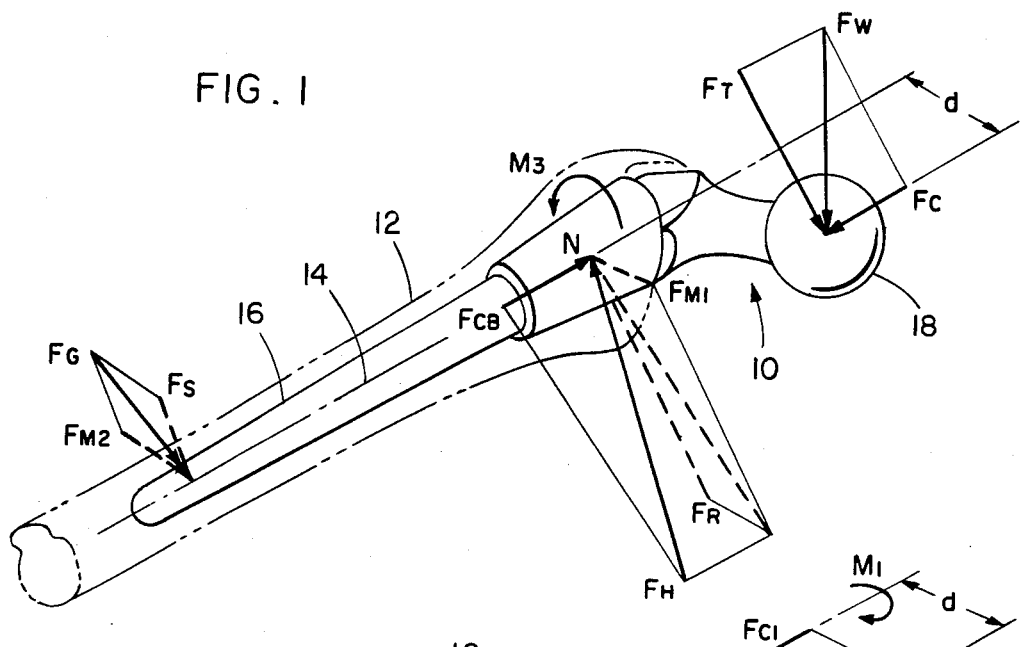
FIG. 1 is an oblique view of a femoral prosthesis of an artifical hip joint showing a typical force system acting on a prosthesis of the present invention, including the reaction forces exerted on the prosthesis by the femur.

With reference now to the drawings, wherein like reference characters designate like or corresponding parts throughout the several views, there is shown in FIG. 1 a diagrammatic representation of a typical force system acting on the femoral prosthesis 10 of an artificial hip joint. The femur 12 is shown inclined at approximately a 30° angle to the horizontal, a position corresponding to that of a person arising from a chair. This discussion will treat static forces only, because they well illustrate the principles involved. Also, the plane through the centerline 14 of the femoral stem 16 and the center of sphere 18 is perpendicular to a vertical plane through centerline 14. Also, for purposes of discussion the reaction forces between the prosthesis 10 and femur 12 are shown acting at a point where they are in fact each distributed over some surface area.

The force $F_W$ being transmitted from the hip joint socket, not shown, to the femur acts vertically downward at the center of sphere 18. In the vertical plane containing $F_W$ and parallel to centerline 14, $F_W$ can be replaced by two components $F_C$ and $F_T$, where $F_C$ is parallel to centerline 14 and $F_T$ at 90° to $F_C$ lies in a plane perpendicular to centerline 14.

Figure 2:
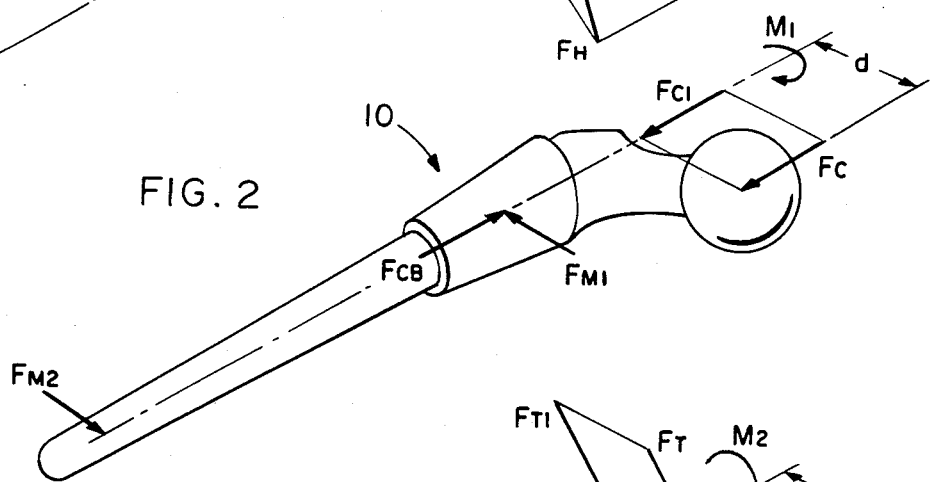
FIG. 2 is the prosthesis of FIG. 1 showing the force system components acting in the plane through the centerline of the stem and the center of the sphere.

Reaction forces exerted by the femur 12 on femoral prosthesis 10 in resisting forces $F_T$ and $F_C$ are assumed to act on centerline 14. These reactions can be analyzed separately and sequentially in the appropriate planes. FIG. 2 shows the reaction forces to $F_C$ acting in the plane through centerline 14 and the line of action of force $F_C$. Here, $F_C$ can be replaced by $F_{C1}$ acting on centerline 14 and the moment $M_1$ which equals $F_C \times d$. This system is resisted by the reaction force $F_{CB}$ and a couple whose forces $F_{M1}$ and $F_{M2}$ act perpendicular to centerline 14 at opposite ends of the implanted prosthetic stem as shown. $F_{CB}$, $F_{M1}$ and $F_{M2}$ are forces exerted on the prosthesis 10 by the femur 12.

Figure 3:
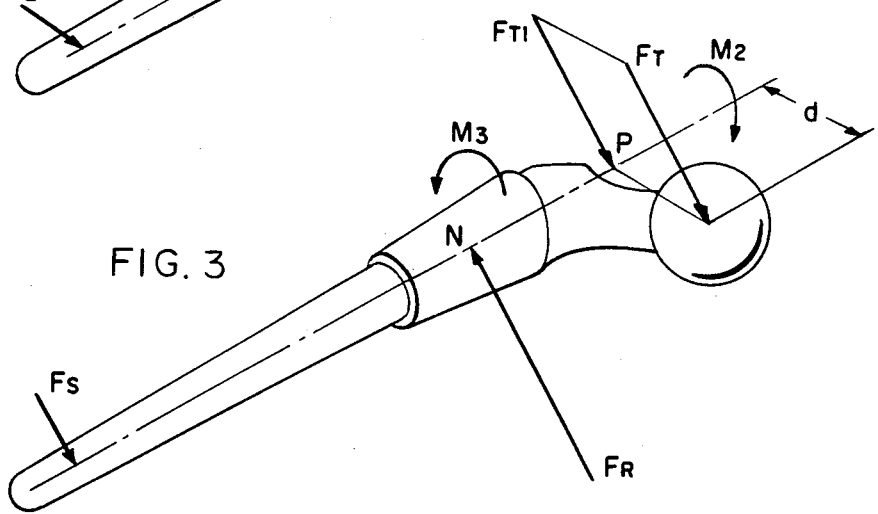
FIG. 3 is the prosthesis of FIG. 1 showing the force system components acting in a vertical plane through the centerline of the stem.

In FIG. 3, first consider the forces acting in the plane containing the line of action of force $F_T$ and prependicular to centerline 14, here force $F_T$ of FIG. 1 can be replaced by its equivalents, force $F_{T1}$ acting perpendicular to centerline 14 at P, a moment $M_2$ which equals $F_T \times d$. Moment $M_2$ works on stem 16 of the prosthesis 10 and sets up the equal and opposite reaction moment $M_3$ exerted by the bone on the prosthesis at the area of interface most resistant to rotation of the stem within the femur 12. This area is specified to be concentrated at point N.

In FIG. 3, next consider the forces in the vertical plane through the line of $F_{T1}$ and the centerline 14, here we show one reaction force $F_R$ to be near the proximal end of femur 12 at point N. A summation of moments reveals that the remaining bone reaction force $F_S$ will vary inversely as the length of stem 16. A summation of forces perpendicular to centerline 14 reveals that reaction force $F_R$ is equal to $F_{T1}$ plus $F_S$. Therefore, a short stem will cause the greater reaction at $F_R$ and is undesirable.

Again, with reference to FIG. 1 in combining forces $F_{M2}$ and $F_S$ at the distal end of prosthesis 10 graphically, one sees the net reactive force at this point to be $F_G$. Combining forces $F_R$, $F_{M1}$ and $F_{CB}$ at the proximal end of prosthesis 10 one sees the net reactive force at point N to be $F_H$. In addition, one sees that the reaction moment $M_3$ will exist at the proximal end of the femur 12 provided the prosthesis 10 is designed to transmit torque to the bone at this point, and only this point.

From the above it is clear that the forces and torque which are transmitted from the prosthesis to the proximal femur may be considerably greater than those transmitted at the distal end of the prosthesis. This situation is advantageous if the prosthesis is designed to transmit the larger forces to the proximal bone in a manner which the bone accepts favorably. One thrust of this invention is that the proximal bone will best accept large forces from the prosthesis when the prosthesis is so configured so as to diffuse or dissipate large forces into a large volume, or against a large area, of bone, both cancellous and cortical. When these large forces are so diffused to load the proximal bone of the femur within its normal physiological stress limits, the bone will respond by maintaining an adequate volume and density or by remodelling to have a volume and density which is greater than that attained over time with prior art devices.

Figure 4:
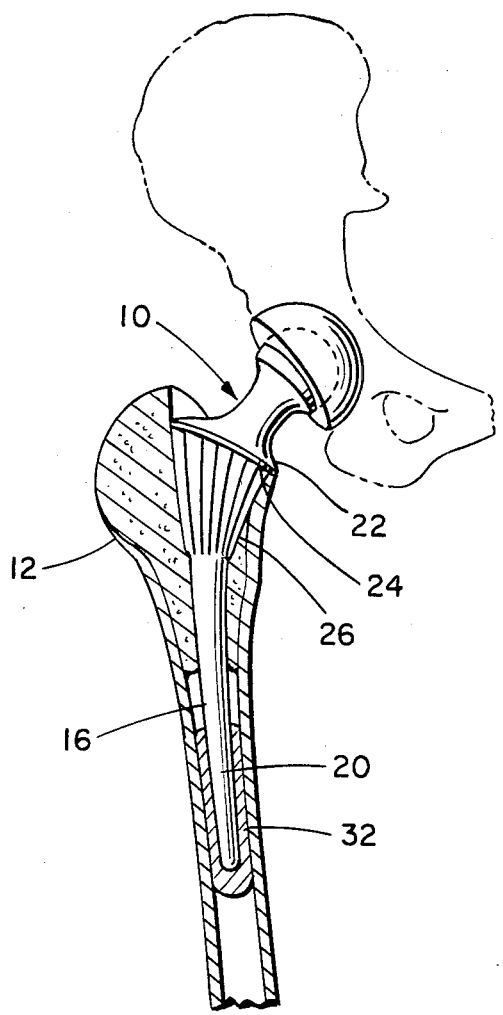
FIG. 4 is a general view of an implanted artifical hip joint embodying the teachings of the present invention.

FIG. 4 shows a femoral prosthesis 10 of an artifical hip joint implanted in femur 12 according to the teachings of the present invention. Preparation of the femur 12 includes excising the neck of the femur at a surface which will abut the undersurface 24 of collar 22 when the prosthesis is implanted, reaming and broaching the femoral canal to accept the stem 16 of the prosthesis, and broaching slots in the proximal cancellous bone of femur 12 to accept the longitudinal fins 26 which extend distally on stem 16 from collar 22. Fins 26 may alternatively be termed as ribs, splines, flutes, keys, etc. as long as the result is an external geometric pattern of elongated projections.

Figure 13:
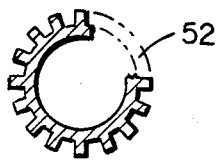
FIG. 13 is a section through the sleeve of FIG. 8 along the line XIII—XIII.
Figure 13:
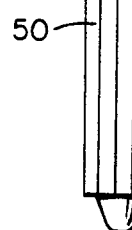

The fins 26 have a thickness as small as is reasonable to manufacture and handle without damage, approximately in the range from 0.5 to 2 mm. The fins 26 have a height of at least 0.7 mm and the spaces between the fins are approximately 1 to 4 mm. It is to be emphasized that the fins provide a primary force transmitting interface of this invention, and that this is different from the bone-to-prosthesis interface of the so-called bone ingrowth concepts using porous materials, because according to the invention interdigitation is created at the time of implant, and the bone projections within the geometric envelope of the surface of the finned part of the prosthesis have a minimum width of 1 mm and a minimum height of approximately 0.7 mm. Further, these bone projections have a length dimension longitudinally of the fins of 10 or more times their width. That is, their length may be 10, 20, 30 mm or more. Further still, in the annulus space 52 in FIG. 13 where bone and fins are interdigitated when the prosthesis is implanted, the ratio of volume space occupied by bone to that occupied by fins is always greater than 1 to 1, and may be as high as 5, 6 or 7 to 1. Indeed, the theoretically ideal ratio of respective volumes in the interdigitated space is the inverse of the strengths of the two materials, or for bone and implant grade metals, approximately 20 or 25 to 1.

In contrast, bone ingrowth into porous material takes at least several weeks and the bone projections into the pores have a maximum dimension of 0.5 to 1 mm in any direction. The porous material in U.S. Pat. No. 3,855,638 specifies a maximum porosity of 40%. Therefore, where the bone and porous material occupy the same space, the ratio of volume space occupied by bone to that occupied by metal is always less than 1 to 1. The mechanics of the porous metal to ingrown bone is ot efficient, because the metal is stronger than the bone by approximately 20 to 1 on a volume basis.

In the preparation of the femur 12 preferably each cavity in the bone is cut slightly smaller than the part of the prosthesis which will fit in the corresponding part of the cavity. Bone will accept the prosthetic elements so driven into undersized cavities, albeit at a great spread of allowable dimensional interference. The soft cancellous bone will easily yield to accept prosthetic intrusion, while the hard cortical bone of the femoral shaft will yield only slightly, and can be split if asked to accept too great an interference fit.

The size relationship of the elements of the prosthesis to the bone of FIG. 4 are very important. Collar 22 preferably has a size and shape to cover the entire area of excised bone in contact with the undersurface of the collar at 24. The envelope of the volume of the fins 26 preferably corresponds closely to the size and shape of the cancellous bone at the proximal end of femur 12. The cross section of the femur in this area is more elliptical than round, having a larger diameter medially to laterally than anteriorly to posteriorly. Accordingly, the envelope of the flutes should be elliptical on the same axes. It is preferred that the flutes fill the cancellous bone space sufficiently that the outer edges of the flutes contact some cortical bone of the wall of the femur, especially at the anterior, posterior and medial aspects. The distal stem 20 must fit within the shaft of femur 12 so that there is no transverse movement or looseness in any direction. Preferable the stem 16 fits tightly in the canal of the femur as a result of femoral reaming and prosthesis size selection. FIG. 4, however, shows an alternate implantation technique where the distal stem 20 is held securely within the femoral canal by the use of PMMA cement confined to the area 32. As explained above for the inventive construction, forces transferring from the prosthesis 10 to the femur 12 are much smaller at the distal end than at the proximal end of the prosthesis. Under this circumstance, the PMMA cement will provide satisfactory long term security of fixation of the distal stem 20 within the canal of femur 12. Further, the invention tends to create minimal axial shear and torque loads on cement so used.

Figure 5:
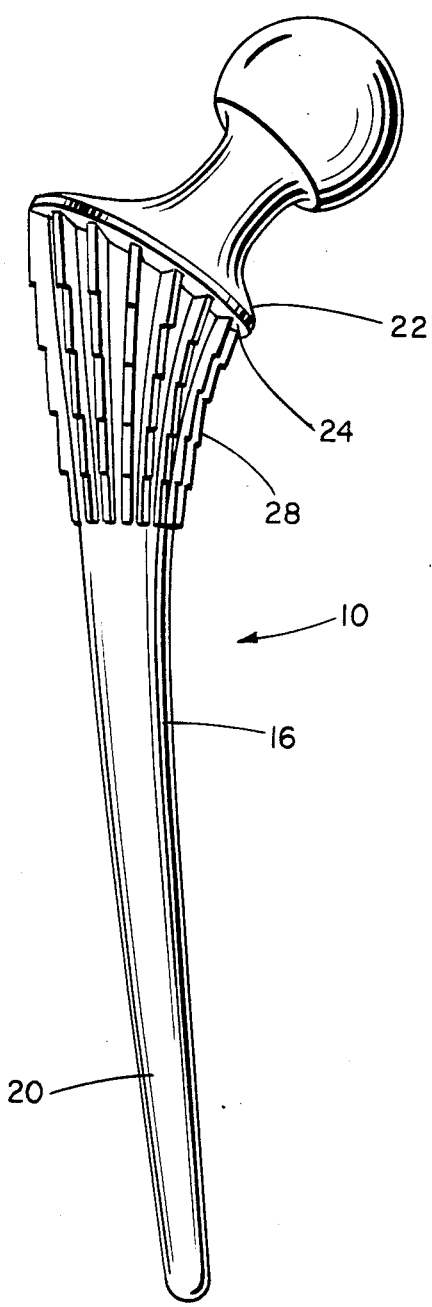
FIG. 5 is a detail view of a prosthesis of the proximal femur showing self-broaching longitudinal flutes according to the present invention.

FIG. 5 shows a detail view of the femoral prosthesis 10 where the fins at 28 are designed to be self-broaching so as to cut their own path into the cancellous bone of the proximal femur. FIGS. 4 and 5 are generalized drawings to illustrate the principles of the invention.

Refer to FIGS. 6 through 11 which show alternative preferred embodiments where collar 122 and flutes 126 and 128 are attached to the thin wall conical sleeve 34. In this case, the femoral prosthesis 40 has no collar or fins, but rather has the conical taper 42 which fits within the tapered inner bore 36 of sleeve 34 by the well known principle of self-locking tapers. In the implanted condition of FIG. 6, the sleeve 34 and the stem of prosthesis 40 are locked together as a single unit and will respond to the applied force system as described above.

This embodiment provides numerous practical advantages. To cover a range of size and shapes of femurs 12, fewer sizes of femoral prostheses 40 are required when compared with the construction of FIG. 5. A large assortment of fluted sleeves 34 is required to permit selection of optimum fit in the proximal femur. The sleeves 34 are much cheaper and smaller than the prostheses 10 or 40, however, and therefore present much less of an inventory problem for the manufacturer and the user. The sleeve 34 may be fabricated from porous metal, or have its outer surfaces coated or treated by any of a number of techniques designed to enhance fixation to bone. The prosthesis 40 becomes an uncompromised structural member, and can be designed and fabricated to that purpose. The procedure for implantation is facilitated for the surgeon, because it can be done in a sequence of simple steps.

Figure 6:
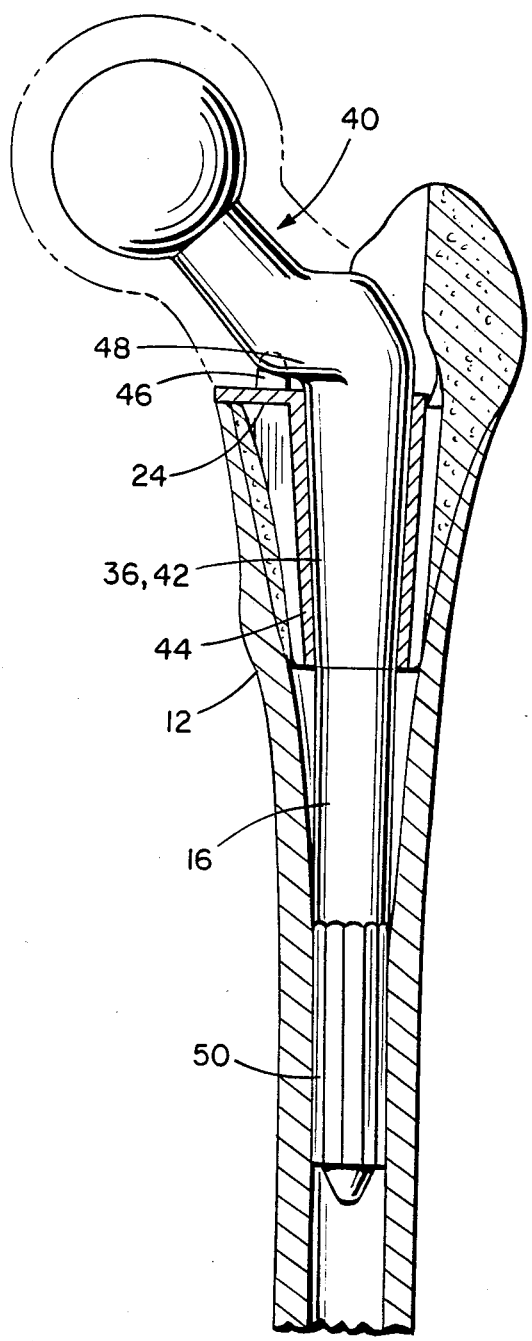
FIG. 6 shows an alternate form of the present invention, used for implantation and fixation of a femoral prosthesis.
Figure 7:
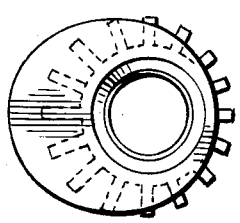
FIG. 7 in a plan view of an alternate form of the thin wall fluted sleeve shown in FIG. 6.

To implant the prosthesis embodiment of FIG. 6, the surgeon excises the head and neck of the femur to provide access to the femoral canal. The canal is reamed to a depth and diameter to accept the stem 16 of the prosthesis 40. Reamers are provided which are matched to the lengths and diameters of the several prosthesis stem sizes available. The reamer also removes bone to accommodate the wall thickness of sleeve 34. Generally, the surgeon will select the largest reasonable stem size which will fit within a given femur. An appropriately designed instrument, located in the reamed canal, is used to cut the proximal surface of the femur around the canal at 90° to the centerline of the reamed canal. This surface will then abut accurately with the undersurface of the collar 24 when the fluted collar is driven into position. A multi-fluted broaching tool can be used to prepare a bed for the fluted sleeve 34, where each groove cut in the femoral bone will be slightly smaller than the corresponding flute which will fit in the groove. Of course, the broached grooves must be in correct angular orientation for the construction of FIG. 6 where anti-rotational lugs 46 engage the shoulder 48 of prosthesis 40. Anti-rotation lugs 46 may be furnished as an assurance to the surgeon, but they are not necessary to prevent rotation of stem 16 within sleeve 34 when the stem 16 is solidly seated within the taper 36 of sleeve 34.

Figure 12:
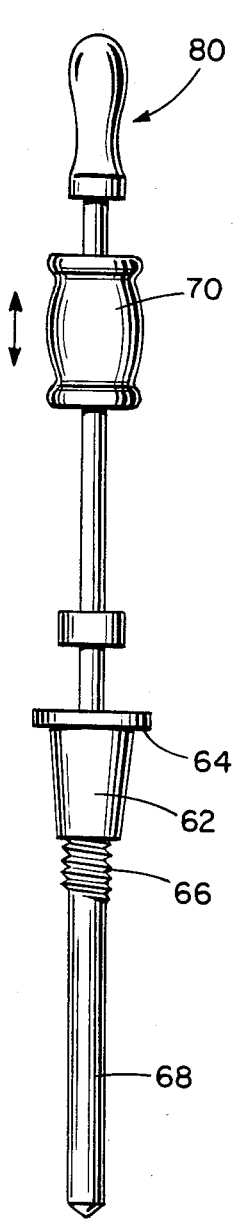
FIG. 12 shows an impact instrument used for implanting the self-broaching sleeve of FIG. 8.
Figure 11:
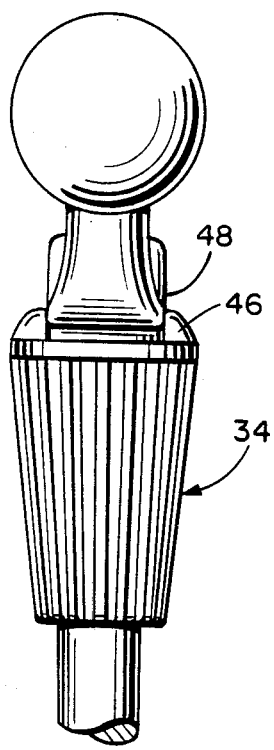
FIG. 11 is an additional view of the sleeve of FIG. 6.
Figure 8:
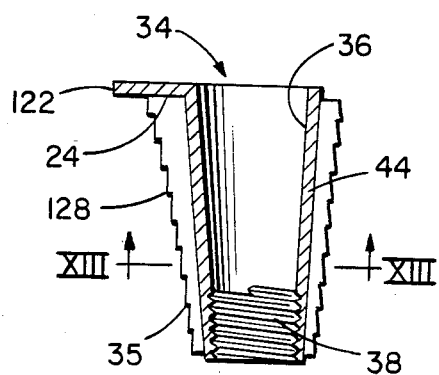
FIG. 8 is a section view of the sleeve of FIG. 7.
Figure 14:
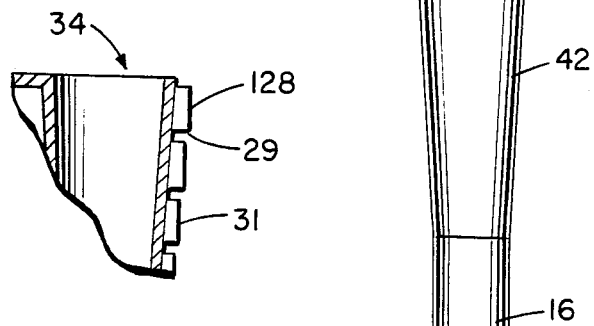
FIG. 14 shows alternative self-broaching flutes on the sleeve of FIG. 8.
Figure 9:
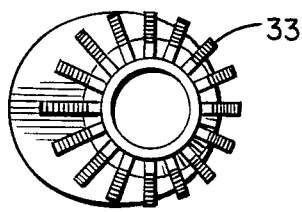
FIG. 9 is another view of the sleeve of FIG. 7.

FIG. 8 shows an embodiment of sleeve 34 with self broaching flutes 128 and a short internal thread 38 at the small end of the tapered bore 36. Each flute or rib 128 is shown to extend the entire length of sleeve 34 and stepped teeth 35 are shown as a means of making the flute self-broaching. Alternatively, the broaching teeth on each longitudinal flute can be formed by cuts or notches 29 shown in FIG. 14 which interrupt the lengthwise continuity of the flute 128. The individual flute segments 31 lie in lengthwise alignment as shown at 33 in FIG. 9. The effective length of an individual flute or rib 128 is specified to be the total length of a series of segments 31 which are in longitudinal alignment, and which segments follow one another into the same space in the bone as the sleeve is being implanted in the bone. This sleeve may conveniently be used with the impact instrument 60 of FIG. 12 for implantation into the proximal femur when the femur has not previously been broached with a fluted broach. Sleeve 34 fits on taper 62 of instrument 60, with collar 22 engaging shoulder 64 and thread 38 engaging thread 66. Stem 68 aligns instrument 60 in the reamed femoral canal. Slide hammer 70 is then reciprocated to drive the fluted sleeve 34 into the proximal femur. Sleeve 34 is available in a series of increasing sizes of envelope of the flutes 28 for each given tapered bore size 36. The surgeon first implants the sleeve with the smallest envelope. The energy required to seat the sleeve gives an indication of the security of seating. If the tightness of fit is judged inadequate, the sleeve is removed by operating the slide hammer 70 in the outward direction. Threads 68 engaged in threads 38 permit the sleeve to be so extracted. The next larger fluted sleeve is implanted, and so on until the surgeon is satisfied that a sleeve 34 is securely fixed in the proximal femur 12. It is recommended that at least four sizes of sleeve be furnished for each stem size, and that the increase in sleeve fin envelope diameter be approximately 1.5 mm per size.

Figure 10:
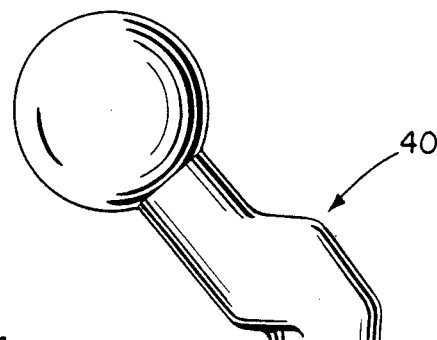
FIG. 10 is a detail view of the femoral prosthesis of FIG. 6.

When a sleeve 34 has been securely seated in the proximal femur, the surgeon selects a femoral prosthesis 40 of correct taper diameter 42 and of diameter of distal stem 50 to fit securely with the reamed femoral canal. The distal end of stem 16 of FIGS. 6 and 10 is shown with longitudinal flats 50. These flats are designed to increase the latitude of diametral fit of the stem in the bone for which there will be no lateral motion between the stem and the bone, and to reduce the hazard of splitting the femoral shaft by an overly tight fit. The distal end 50 of the stem 16 is made with a smooth surface and not intended to transmit axial shear load from the stem to the bone and not intended to transmit torque from the stem to the bone.

Should there be any reason for the distal stem 50 to not engage securely with the femoral canal, the surgeon may elect to place PMMA cement in the canal in the area indicated at 32 in FIG. 4 prior to the final insertion of the femoral prosthesis 40, and the prosthesis is driven solidly into engagement with the internal taper 36 of sleeve 34. Again, it must be emphasized that cement is not used in the cancellous bone of the proximal femur. Note that in the sequence just described, the finned sleeve is fully implanted before cement would be delivered to the femoral canal for anchoring the distal stem. This sequence prevents cement from entering the interface between the fins and the cancellous bone.

The femoral prosthesis 40 implanted according to the above description is fixed to the femur with adequate strength to permit early physical therapy and rehabilitation of the patient. The pattern of load transfer to the femur creates stresses which favor the retention of and development of sound bone in proximal femur, and increased activity by the patient will tend to improve the bone structure in accordance with the above.

Although the invention has been shown and described with reference to preferred embodiments, various changes and modifications will appear obvious to one skilled in the art; such are deemed to come within the purview of the present invention.

What is claimed is:

1. A joint prosthesis component means for fixation to bone, comprising:

first means defining a joint motion surface;

a stem attached to said first means defining a joint motion surface for extending into the central canal of the bone into which the component means is to be fixed;

that part of the prosthesis component means which is intended to be located within the bone at the end of bone near the joint motion surface defining an external geometric pattern of elongated projections spaced circumferentially around said prosthesis component means which engage with the bone when implanted in the bone, said elongated projections having a thickness of from about 0.5 mm to about 2.0 mm, a height of at least about 0.7 mm, a spacing of from about 1 mm to about 4 mm and an effective length at least ten times their thickness; and the effective length of said external geometric pattern of elongated projections is less than one half of that portion of the prosthesis component means which is intended to be implanted within the bone.

2. A joint prosthesis component means according to claim 1 wherein said elongated projections define broaching means that establishes a tight fit and prevents rotation between said prosthesis component means and said bone when said prosthesis component means is driven and fixed into said central canal of the bone.

3. A joint prosthesis component means according to claim 1 wherein a collar is formed at a proximal end of said projections and extending circumferentially beyond said projections so as to seat against a resected surface of said bone.

4. A method for fixation of a joint prosthesis component means to a bone comprising the steps of:

preparing the central canal of a bone forming part of a body joint at the end thereof near the body joint to receive a stem of a joint prosthesis component means having a joint motion surface, a stem to be received in the central canal of the bone, and an external geometric pattern of effectively elongated projections;

cutting a geometric pattern of elongated cavities in the central canal of the bone at said end near the body joint, said cavities having an inverse related geometry to the external geometric pattern of effectively elongated projections to the prosthesis component means to enable interdigitation of the projections with the bone with zero clearance between the projections and cavities wherein said effectively elongated projections are spaced circumferentially around said central canal and said projections have a thickness of from about 0.5 mm to about 2.0 mm, a height of at least about 0.7 mm, a spacing of from about 1 mm to about 4 mm and an effective length at least ten times their thickness and wherein the effective length of said external geometric pattern of effectively elongated projections is less than one half of that portion of the prosthesis component means which is implanted within the bone; and fixing the prosthesis component means to said bone by inserting the stem thereof into the prepared canal and forcing the projections into the cavities in engagement with the bone with sufficient security to have the prosthesis component means implanted in the bone.

5. The method according to claim 4 wherein the steps of fixing said prosthesis component means includes broadening said central canal with said elongated projections when said prosthesis component means is driven into said central canal.

6. The method according to claim 4 wherein the preparation of the central canal includes the step of excising a portion of the end of the bone transversely to the canal axis and providing a collar at the end of the elongated projections near the joint motion surface which contacts the excised end of the bone and which is shaped and sized to substantially cover same.

7. The method according to claim 4 including the further step of cementing the stem in the canal at a distal end remote from the joint motion surface.

* * * * *